United States Patent [19]
Martin

[11] Patent Number: 5,961,971
[45] Date of Patent: Oct. 5, 1999

[54] **BIOCONTROL OF FUNGAL SOILBORNE PATHOGENS BY *PYTHIUM OLIGANDRUM***

[75] Inventor: Frank N. Martin, Salinas, Calif.

[73] Assignee: University of Florida, Gainesville, Fla.

[21] Appl. No.: 08/731,722

[22] Filed: Oct. 17, 1996

[51] Int. Cl.$^6$ .............................. A01N 63/00; A01N 3/00; C12N 1/14
[52] U.S. Cl. ...................... 424/93.5; 435/254.1; 504/117
[58] Field of Search .................................. 424/93.1, 93.5; 435/254.1; 504/116, 117

[56] References Cited

U.S. PATENT DOCUMENTS

| | | | |
|---|---|---|---|
| 4,259,317 | 3/1981 | Vesely et al. | 424/93.5 |
| 4,574,083 | 3/1986 | Baker et al. | 424/93 |

OTHER PUBLICATIONS

Martin "Selection of DNA probes useful for isolate identification of two Phythium spp.", Phytopathology (1991) 81: 742–746.
Martin et al. "The use of *Pythium oligandrum* for biological control of pre–emergence of damping–off caused by P. ultimium", Phytopathology (1987) 77: 1013–1020.
Martin et al. "Biological control of damping–off of tomato transplants using non–plant pathogen *Pythium oligandrum*" Phytopathology (1991) 81(10): 1149.
Martin et al. "Efficacy of *Pythium oligandrum* in field evaluations for controlling damping–off of tomato transplants", Phytopathology (1994) 84(10): 1113.
Martin et al. "Selection of fungicide tolerant isolates of *Pythium oligandrum*" Phytopathology (1985) 75(11): 1327.
Vesely "Potential biological control of damping–off pathogens in emerging sugar beet by *Pythium oligandrum* Drechsler", Phytopath. Z. (1977) 90: 113–115.
Whipps, J., "Status of Biological Disease Control in Horticulture," Biocontrol Science Tech. (1992) 2: 3–24.
Al–Hamdani, A.M., R.S. Lutchmeah, R.C. Cooke (1983)"Biological control of *Pythium ultimum*–induced damping–off by treating cress seed with the mycoparasite *Pythium oligandrum*" Plant Pathology 32:449–454.
Ayers, W.A., R.D. Lumsden (1975) "Factors Affecting Production and Germination of Oospores of Three Pythium Species"Phytopathology 65:1094–1100.
Bratoloveanu, J., H.R. Wallace (1985) "The influence in Pythium on the growth of barley seedlings as affected by soil water and inoculum density" Plant and Soil 85:305–311.
Deacon, J.W. (1976) "Studies On *Pythium oligandrum*, An Aggressive Parasite Of Other Fungi" Trans. Br. mycol. Soc. 66(3):383–391.
Drechsler, Charles (1946) "Several Species Of Pythium Peculiar In Their Sexual Development" Phytopathology 36:781–864.
Kilpatrick, R.A. (1968) "Seedling Reaction Of Barley, Oats, And Wheat To Pythium Species" Plant Disease Reporter 52(3):209–212.
Klemmer, Howard W., Richard Y. Nakano (1964) "Distribution And Pathogenicity Of Phytophthora And Pythium In Pineapple Soils Of Hawaii" Plant Disease Reporter 48(11):848–852.
Lutchmeah, R.S. and R.C. Cooke (1984) "Aspects Of Antagonism By The Mycoparasite *Pythium oligandrum*" Trans. Br. mycol. Soc. 83(4):696–700.
Lutchmeah, R.S. and R.C. Cooke (1985) "Pelleting of seed with the antagonist *Pythium oligandrum* for biological control of damping–off" Plant Pathology 34:528–531.
McQuilken, M.P., J.M. Whipps, R.C. Cooke (1990) "Control of damping–off in cress and sugar–beet by commerical seed–coating with *Pythium oligandrum*" Plant Pathology 39:452–462.
O'Sullivan, E. and J.A. Kavanagh (1992) "Characteristics and pathogenicity of Pythium spp. associated with damping–off of sugar beet in Ireland" Plant Pathology 41:528–590.
Walther, D. and D. Gindrat (1987) "Biological Control of Phoma and Pythium Damping–Off of Sugar–Beet with *Pythium oligandrum*" J. Phytopathology 119:167–174.

*Primary Examiner*—Jean C. Witz
*Assistant Examiner*—Susan Hanley
*Attorney, Agent, or Firm*—Saliwanchik, Lloyd & Saliwanchik

[57] ABSTRACT

Described are non-phytopathogenic *Pythium oligandrum* isolates having activity to control phytopathogenic Pythium spp. or control damping-off of a plant, by applying an effective amount of the non-phytopathogenic isolates to a plant or its situs. The isolates can be applicable crops utilizing transplant systems. Also described are methods of using the isolates and genetic sequences identified from the isolates which can be useful in identification procedures.

16 Claims, 1 Drawing Sheet

BIOCONTROL OF FUNGAL SOILBORNE PATHOGENS BY *PYTHIUM OLIGANDRUM*

BACKGROUND OF THE INVENTION

Within the fungal genus Pythium are plant pathogenic species which can cause significant losses in vegetable production. The value of vegetable crops grown in the state of Florida totaled over $1.79 billion for the 1991–92 crop season with much of the cabbage, cucumber, pepper, and tomato crops planted as transplants. Tomato alone accounts for $735 million in this production total and over 80% of the crop is transplanted. The use of vegetable transplants in commercial field production systems is important in many areas of the United States. In California, all of the celery, fresh market tomato and pepper, and most of the cauliflower and broccoli are grown as transplant crops. In Monterey County alone, the value of the transplants grown in 1992 amounted to nearly $18 million and represented a final crop value of $176 million.

Plant pathogenic Pythium species can kill a plant at the seedling stage or can reduce crop yield by destroying the root system of a mature plant. While diseases in the seedling stage are often controlled by fungicide application, the continued use of certain highly effective fingicides, e.g., metalaxyl, has faced regulatory uncertainty for use in vegetable transplant greenhouse production systems. In addition, continued use of a particular fungicide can result in the development of tolerance by the pathogen. Fumigants such as methyl bromide, which are routinely used on high cash-value crops, also face regulatory uncertainty. Thus, disease control (in particular damping-off) in the production greenhouses as well as in the field following transplanting are a major concern.

In addition to the plant pathogenic species of Pythium, some members of this genus exist strictly as soil saprophytes (Van der Plaats-Niterink, 1981, Monograph of the genus Pythium. Studies in Mycology No. 21. Centraalbureau Voor Schimmelcultures, Baarn, The Netherlands), and several have been identified that are pathogenic on mammals (de Cock et al., 1987, J. Clin. Micro. 25:344–349), fish (Van der Plaats-Niterink, 1981), and insects (Saunders et al, 1988, J. Invert. Path. 52:360–363). One species, *Pythium oligandrum* Drechsler, is not pathogenic on plants and is effective in protecting plants from attack by pathogenic species.

An alternative to the use of pesticides for controlling phytopathogenic Pythium spp. is the use of biological control agents for vegetable transplants, a large and expanding industry in which disease protection is needed in the greenhouse as well as in the field after transplanting.

U.S. Pat. No. 4,574,083 to Baker and Lifshitz describes *Pythium nunn*, which is not pathogenic to plants and can protect seedlings from damping-off in greenhouse evaluations. However, *P. nunn* generally grows slower in culture medium than *P. oligandrum* but, in contrast to *P. oligandrum*, can colonize organic substrates in the soil that have already been colonized by other fungi. *Pythium nunn* also can be difficult to sporulate; sporulation is an essential characteristic for inoculum production. In the soil, *P. nunn* also behaves differently than *P. oligandrum* in that, as a primary colonizing saprophyte, it is not as aggressive.

There are a number of studies examining the effect of seed treatment with oospores of *P. oligandrum* on reducing subsequent levels of disease, most of which have been conducted in the greenhouse. Deacon (1976; Trans. Br. Mycol. Soc. 66:383–391) described the ability of mycelial seed coatings on wheat to significantly reduce the disease incidence over untreated seeds.

Vesely (1977; Phytopath Z. 90:113–115; 1979) observed that application of oospores to sugarbeet seed reduced damping-off incidence to a similar level as thiram treatment (see also Schippers, B. and W. Gams, eds. Academic Press, *Soil-Borne Plant Pathogens*). In U.S. Pat. No. 4,259,317, Vesely et al describe the application of *Pythium oligandrum*, or "Polygandron." However, the '317 patent describes a particular isolate *P. oligandrum* for protecting against damping-off by applying a preparation to sugarbeet seed. There is no description or suggestion in the '317 patent regarding the use of Polygandron on vegetable transplants.

A co-worker and I observed a similar response for disease control when using isolates of *P. oligandrum* recovered from suppressive soils pelleted onto sugarbeet seeds. See Martin and Hancock (1987; Phytopathology 77:1013–1020). While the emerging radicle was colonized by the biocontrol agent and protected from plant infection, this colonization was limited to association with the seed coat and suggested that the fungus was not rhizosphere competent. Additional greenhouse trials on cress (Al-Hamdani et al, 1983, Plant Pathology 32:449–454; McQuilken et al., 1990 Plant Pathology 39:452–462, 1992 J. Phytopathol 135:125–134); sugarbeet and carrot (Lutchmeah and Cooke, 1985, Plant Pathology 34:528–531); and sugarbeet (Walther and Gindrat, 1987, Journal of Phytopathology 119:167–174) have indicated that seed treatment with *P. oligandrum* can control other phytopathogenic Pythium spp., *Phoma betae*, and *Mycocentrospora acerina*.

A biological agent that could protect seedlings from disease in the production facility and after transplanting into the field would meet an existing need and provide an advantageous method for controlling disease, e.g., damping off, in agricultural industries.

BRIEF SUMMARY OF THE INVENTION

The subject invention concerns novel isolates of *P. oligandrum* that can be used successfully as a biological control agent capable of protecting crops from disease caused by pathogenic fungal species, including pathogenic Pythium species. Advantageously, the isolates of the subject invention lack pathogenicity on crop plants, have a similar ecology as some pathogenic species, can readily produce inoculum, and are efficacious in controlling disease. Other isolates of this species were found to be associated with soils suppressive to a pathogenic species.

Amendment of field soil naturally infested with phytopathogenic Pythium spp. with oospores of *P. oligandrum* can also reduce the incidence of disease when cropped to susceptible hosts in the greenhouse (Martin and Hancock, 1987). We have conducted field trials evaluating efficacy in vegetable transplants in Florida and have identified isolates that are as effective as metalaxyl in protecting against phytopathogenic Pythium spp. when added to seedlings prior to transplanting.

It should be emphasized that although the biocontrol agent is in the same genus as many of the pathogens that it is capable of controlling, the isolates examined are not pathogenic on any of the crops that have been tested (Drechsler, 1946, Phytopathology 36:781–864; See also Example 7 herein below). Molecular markers to confirm the identification of the biocontrol isolates as *P. oligandrum* have been identified. See example 6, below.

Advantageously, the subject fungus occupies a similar ecological niche as the pathogens and is vegetatively active under similar soil pH, temperature, and moisture regimes. It has an extensive ecological range and has been recovered from a variety of cultivated and noncultivated soils throughout the world. This is an indication of the range of environmental conditions in which it can survive. In addition, such a ubiquitous nature of the subject isolate can ease regulatory concerns regarding the introduction of organisms into areas in which they have not previously been reported. The fungus sporulates readily, and large amounts of oospore inoculum can be produced by either liquid or solid substrate fermentation. These oospore preparations can be capable of prolonged survival for extended periods of time. In vitro experimentation and greenhouse trials suggest that *P. oligandrum* also can be effective in controlling other soilborne diseases.

Due to similarity in growth conditions in commercial production facilities, and in some cases types of soilless mix used in production, *P. oligandrum* also can be useful for controlling disease in ornamental container crops.

The subject invention also concerns novel methods of production which advantageously result in an efficacious inoculum.

In addition, the subject invention includes novel nucleotide sequences which can be useful as isolate-specific markers or can be labeled by employing standard procedures or techniques for use as probes. It is well recognized in the art that isolated nucleotide sequences can have other utilities, including non-specific uses that include their use as a molecular weight marker in nucleic acid size determination assays.

BRIEF DESCRIPTION OF THE SEQUENCES

SEQ ID NO. 1 shows the nucleotide sequence comprising a unique region and flanking regions of an inverted repeat delimited by PstI restriction sites from mitochondrial DNA from *Pythium oligandrum* isolate 1982-24. A small unique region is present from bases 1278–2649, inclusive.

SEQ ID NO. 2 shows the nucleotide sequence comprising a unique region and flanking regions of an inverted repeat delimited by PstI restriction sites from mitochondrial DNA from *Pythium oligandrum* isolate 1985-5. A small unique region is present from bases 1281–2653, inclusive.

SEQ ID NO. 3 shows the nucleotide sequence comprising a unique region and flanking regions of an inverted repeat delimited by PstI restriction sites from mitochondrial DNA from *Pythium oligandrum* isolate 1986-41. A small unique region is present at bases 1281–2653, inclusive.

SEQ ID NO. 4 shows the nucleotide sequence comprising a unique region and flanking regions of an inverted repeat delimited by PstI restriction sites from mitochondrial DNA from *Pythium oligaandrum* isolate 17-1. A small unique region is present at bases 504–715, inclusive.

SEQ ID NO. 5 shows the nucleotide sequence comprising a unique region and flanking regions of an inverted repeat delimited by PstI restriction sites from mitochondrial DNA from *Pythium oligandrum* isolate 23-5. A small unique region is present at bases 502–684, inclusive.

SEQ ID NO. 6 shows the nucleotide sequence comprising a unique region and flanking regions of an inverted repeat delimited by PstI restriction sites from mitochondrial DNA from *Pythium oligandrum* isolate 1986-42. A small unique region is present at bases 270–664, inclusive.

SEQ ID NO. 7 shows the nucleotide sequence comprising a unique region and flanking regions of an inverted repeat delimited by PstI restriction sites from mitochondrial DNA from *Pythium oligandrum* isolate 27-6. A small unique sequence is present at bases 504 to at least base 565, inclusive.

SEQ ID NO. 8 shows the nucleotide sequence comprising a unique region and flanking regions of an inverted repeat delimited by PstI restriction sites from mitochondrial DNA from *Pythium oligandrum* isolate 30-1. A small unique sequence is present at base 504 to at least base 612, inclusive.

DETAILED DESCRIPTION OF THE INVENTION

Figure 1:
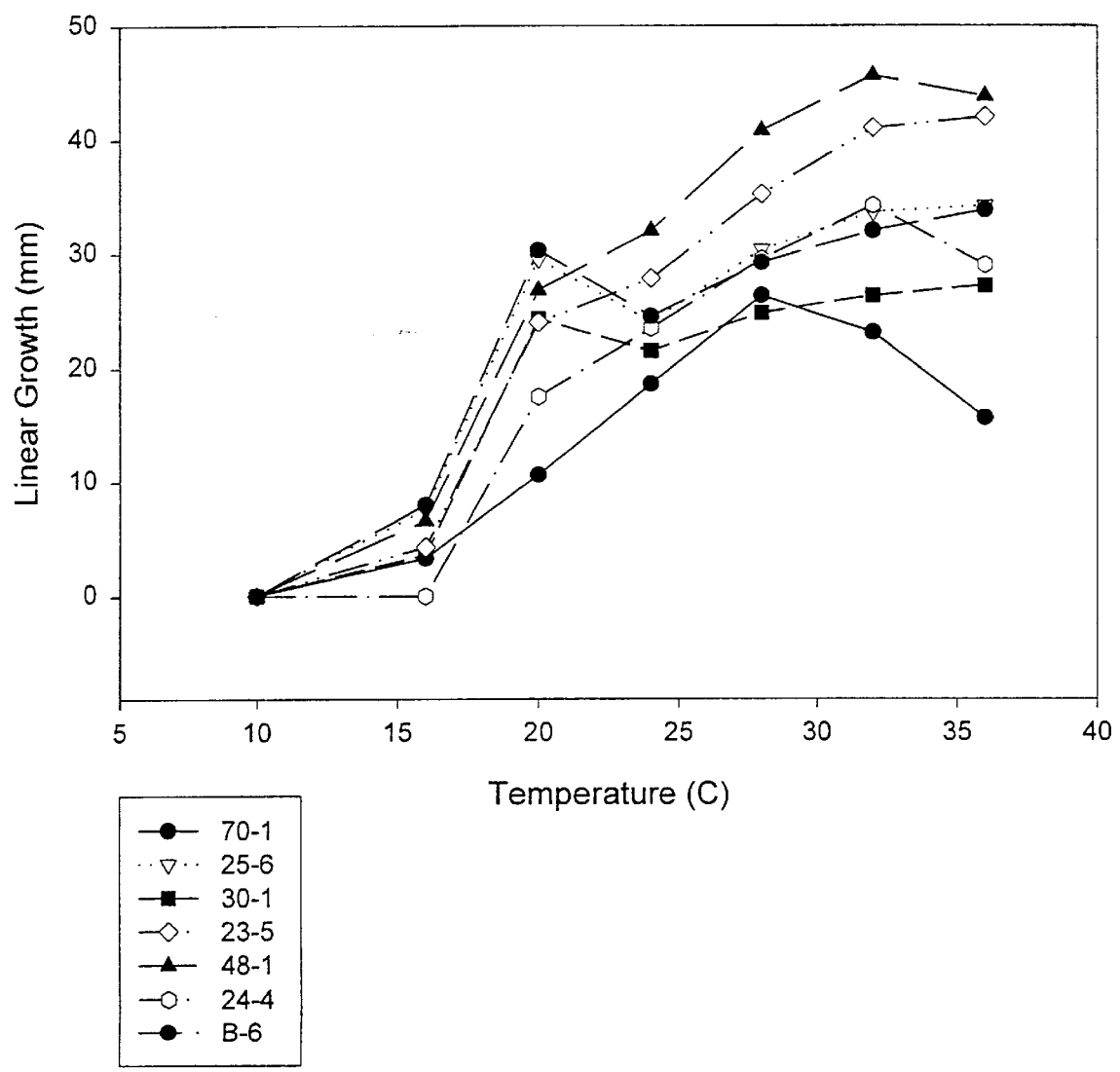
FIG. 1 shows linear growth rates of isolates of *Pythium oligandrum* on corn meal agar for a 24hour period when incubated at the indicated temperatures.

The subject invention relates to a novel, efficacious biocontrol agent comprising a nonpathogenic species, *Pythium oligandrum*. The subject isolate is not pathogenic on plants and shares a similar ecology to the pathogenic species within the same Pythium genus. Therefore, the subject isolates have the advantage of being active under similar environmental conditions and compete for occupation of the same ecological niche as the pathogens. A number of isolates have been evaluated for efficacy in controlling damping-off of tomato transplants. Several isolates have been identified that provided consistent protection from disease in field evaluations over a five-year period.

The *P. oligandrum* of the subject invention are different isolates than the previously-described Pythium species used as biocontrol agents, (e.g., Polygandron described in the aforementioned '317 patent). Another important difference is the different process, e.g., culture medium used to grow the biochemical agent. There is a great deal of variability among isolates, e.g., cultural characteristics (growth rates, response to temperature, spore formation, germination), as well as efficacy in protecting from disease.

Morphological characteristics of the isolates conform to the taxonomic characteristics described for the species (Van der Plaats-Niterink, 1981). For isolates grown on liquid grass blade cultures, sporangia are contiguous, forming irregular aggregates consisting of subglobous elements with connecting filamentous parts. Mostly formed intercalary but occasionally terminal. Zoospores are produced. Oogonia average 25 $\mu$m in diameter and are covered with conical protuberances 5–7 $\mu$m long and 2–3 $\mu$m at the base. Antheridia are generally lacking. Oospores are aplerotic and average 22 $\mu$m in diameter. Cultural characteristics such as linear growth rates and sporulation may be found in FIG. 1 and Table 1, respectively. Details of molecular characterization of isolates as *P. oligandrum* may be found in Example 6.

TABLE 1

Production of sporangia, zoospores, and oospores by select isolates of *Pythium oligandrum* with different levels of efficacy in protecting tomato transplants from damping-off

| Isolate | Sporangia[a] | Zoospores[a] | Oospores[b] |
|---------|--------------|--------------|-------------|
| 70-1    | 7.3 B[c]     | 0            | 66.2AB      |
| 25-6    | 22.9 E       | 5            | 120.1 D     |
| 30-1    | 11.1 C       | 0            | 124.9 D     |
| 23-5    | 11.8CD       | 15           | 79.5BC      |
| 48-1    | 14.6 D       | 10           | 54.5 A      |
| 24-4    | 5.5AB        | 0            | 84.9BC      |
| B-6     | 7.3 B        | 0            | 90.5 C      |

[a]Sporangia counted in field of view of a stereo microscope at 95× of isolates grown on grass blade-water cultures that were five days old. Zoospore discharge was reduced by placing cultures at 4° C. for 30 minutes and allowing to warm up to room temperature.
[b]Oospore counts were made of isolates grown on ½ strength V-8 juice broth for 14 days at 25° C. Values represent average numbers of thick-walled mature oospores counted in field of view of compound microscope at 200× magnification.
[c]Values in the same column followed by the same letter are not significantly different (P = 0.05) as determined by Duncan's multiple range test.

Isolates of the subject invention were deposited with the American Type Culture Collection (ATCC), 10801 University Boulevard, Manassas, Va. 20110-2209. The cultures were assigned the following accession numbers by the repository:

| Culture | Accession number | Deposit date |
| --- | --- | --- |
| *Pythium oligandrum*, isolate 70-1. | ATCC 74395 | October 8, 1996 |
| *Pythium oligandrum*, isolate 25-6. | ATCC 74393 | October 8, 1996 |
| *Pythium oligandrum*, isolate 30-1. | ATCC 74394 | October 8, 1996 |

The subject cultures have been deposited under conditions that assure that access to the culture(s) will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit(s), and in any case, for a period of at least 30 (thirty) years after the date of deposit or for the enforceable life of any patent which may issue disclosing the cultures. The depositor acknowledges the duty to replace the deposit (s) should the depository be unable to furnish a sample when requested, due to the condition of the deposit(s). All restrictions on the availability to the public of the subject culture deposits will be irrevocably removed upon the granting of a patent disclosing them.

Procedures for the production of efficacious inoculum using inexpensive culture media have been developed, as have methods for inoculum formulation to provide a prolonged shelf life. Preliminary data suggest that this biocontrol agent also is capable of protecting several ornamental container crops from damping-off.

In view of its demonstrated efficacy in field trials, *P. oligandrum* can be used for controlling damping-off due to phytopathogenic Pythium spp. in commercial transplant production systems.

Evaluations of *P. oligandrum* as a biological control agent were conducted in Florida. Over 140 isolates have been collected from different geographical regions of the world, many of which have been evaluated for efficacy for protection of transplants in the greenhouse and field (experimentation conducted with APHIS approval and in accordance with their guidelines). Information on the physical and chemical properties of the soils from which many of these isolates were recovered is available. The isolates examined in these investigations have not demonstrated any pathogenicity to the crops tested (a number of different vegetable and grain crops as well as several ornamentals). Extensive molecular genetic characterization of representative isolates also has been done, including analysis of mitochondrial DNA (mtDNA), electrophoretic karyotype of chromosomes, and nbosomal DNA (*Genome* 34:156–162; *Current Genet.* 28:255–234; *Exp. Mycol.* 14:32–46; *Phytopathology* 81:742–746; *Mycologia* 87:333–353). Recent sequence analysis of the mtDNA has identified regions that are variable among isolates and can be useful for the construction of isolate-specific markers (see SEQ ID. NOs. 1–8). It is understood by those of ordinary skill in the art that such nucleotide sequences can also be useful as molecular weight markers or as probes. Probes can be constructed by labeling the nucleotide sequence of interest with a signal-generating moiety or a component of a signal-generating system using techniques that are well recognized in the art.

One advantage of the *P. oligandrum* of the subject invention is that it is compatible with existing grower practices, including the use of fungicides. Genetically stable mutants of some isolates of the biocontrol agent tolerant to several commonly used fungicides have been developed.

In a preferred method, the biocontrol agent of the subject invention is used for vegetable transplants. This is due, for example, to the ease with which such agents can be applied: either mixed into the planting medium prior to seeding or drench applied post-planting, techniques that are well-recognized in the art. In addition, the soilless mix that is typically used as a growth or potting medium is less biologically complex than field soil. Such soilless mix growth medium can facilitate establishment of the biocontrol agent. The vegetable transplant system has a comparatively small volume of potting medium per seedling that has to be treated. Another advantage of this production system is that the biocontrol agent will be established on the seedlings at the time of transplanting into the field. Thus, a single application of the biocontrol agent at the time of planting can protect from disease while the plants are in the production greenhouses as well as when transplanted in the field. Due to similarity in potting medium and greenhouse production systems, the procedure developed for transplant crops also can be useful in ornamental container crops.

Following are examples which illustrate procedures for practicing the invention. These examples should not be construed as limiting. All percentages are by weight and all solvent mixture proportions are by volume unless otherwise noted.

EXAMPLE 1

Greenhouse Screening Trials

The subject isolate has been evaluated in the greenhouse for its ability to protect tomato and cucumber transplants from damping-off caused by *P. aphanidermatum* following planting in field soil. Transplant plugs were infested with a liquid preparation of the biocontrol agent prior to transplanting into field soil naturally infested with phytopathogenic Pythium spp. (primarily *P. aphanidermatum, P. ultimum*, and *P. irregulare*). To ensure that disease levels of untreated controls are between 50–70% seedling death, the soils are infested with additional *P. aphanidermatum* grown in a vermiculite medium. Those isolates that provide a 90% level of control were then tested in the field.

EXAMPLE 2

Field Trials

Field trials were conducted on a research plot naturally infested with the phytopathogenic species *Pythium ultimum, Pythium irregulare,* and *Pythium aphanidennatum.* The population levels were increased to a level which gave approximately 50% death in untreated controls by cropping to susceptible crop varieties and disking under the crop debris. This approach allows for inoculum buildup by pathogenic attack of the host as well as saprophytic buildup through colonization of crop residue. Plots currently have six replicates of 24 plants per treatment. The soil used throughout this investigation was a Chiply sand with 5–10% silt+clay content, 3.72% organic matter, and 238 ppm soluble salts. The native soil pH was 5.3, as determined by measurement of saturation paste after 4 hours incubation. The extractable concentrations of Al, Ca, Cu, Fe, K, Mg, Na, P, and Zn were 979.0, 940.0, 0.61, 37.5, 145.0, 145.0, 9.2, 183.0, 4.32 mg/kg soil, respectively.

Field trials with tomato transplants were conducted for 11 growing seasons with efficacy observed in eight seasons (Table 2); the disease level was high for one season (73% disease in fungicide check) and significant differences among all treatments were not observed in two other seasons.

restricted to the single cell. Cell to cell growth was not observed. Therefore, under aseptic conditions, the subject biocontrol agent is primarily a surface colonizer of the root. When the seedlings were removed from the agar medium and washed prior to plating on fresh culture medium, low rates of recovery of P. oligandrum were observed, even though the fungus was observed microscopically on the root. This low frequency of recoverability may be one reason for not getting higher levels of root colonization from field grown plants as described below.

TABLE 2

Summary of plant death observed during eight planting seasons occurring on tomato seedlings treated with selected isolates of Pythium oligandrum

| | % Death | | | | | | | |
|---|---|---|---|---|---|---|---|---|
| Treatment | Spring 90 | Fall 90 | Spring 91 | Spring 92 | Fall 92 | Fall 93 | Spring 94 | Fall 94 |
| Untreated | 45.8 B | 47.9 D | 37.5 C | 33.3 B | 41.65 B | 41.1 A | 33.3 C | 32.6 A |
| Ridomil | 12.5 AB | 4.0 A | 10.4 AB | 16.8 AB | 35.4 AB | 36.8 AB | 11.1 A | 23.6 AB |
| 24-4 | 8.3 A | 24.9 ABCD | NT | 0 A | 18.7 AB | NT | NT | NT |
| 25-6 | 10.4 AB | 33.3 ABCD | 1.0 A | 6.25 A | 14.5 A | 25.7 AB | 20.8 B | NT |
| 30-1 | 10.4 AB | 12.5 AB | 7.3 AB | 14.6 A | 27.0 AB | 29.9 AB | 18.0 AB | 13.2 B |
| 23-5 | 18.7 AB | 33.3 ABCD | 12.5 B | 2.1 A | 35.4 AB | 25.0 AB | 11.8 AB | NT |
| 70-1 | 4.2 A | 16.6 ABC | 1.0 A | 4.2 A | 37.5 AB | 16.7 B | 11.8 AB | 16.7 B |
| 48-1 | 33.3 AB | 27.1 ABCD | NT | NT | NT | NT | NT | NT |
| B-6 | 27.1 AB | 43.6 BCD | NT | NT | NT | NT | NT | NT |
| C-3 | 22.9 AB | 43.7 BCD | NT | NT | NT | NT | NT | NT |
| 1986-41 | 8.3 A | 22.9 ABCD | 5.2 AB | NT | NT | NT | NT | NT |

Values followed by the same letter are not significantly different according to Duncan's multiple range test (p = 0.05).
NT = isolate not evaluated during this planting season.

Isolate 70-1 from Florida showed the highest efficacy of all isolates tested. This isolate has provided levels of protection identical to fungicide treatments and allowed for significantly higher stand counts than observed in the untreated controls in seven of the eight trials. Isolates 25-6 and 30-1 (both from the Southwest USA) have also been highly efficacious. Variation in efficacy for isolate 25-6 correlated with seasonal effects, having significantly improved stand count in only 33% of the trials conducted in the fall compared to 75% in the spring. While Rhizoctonia solani was occasionally recovered from diseased seedlings, this was at a low level, and the predominant cause of damping-off were phytopathogenic Pythium spp.

In addition to variation in efficacy as a biocontrol agent, there also is a high degree of variation in cultural characteristics among isolates of P. oligandrum. Differences in linear growth rates and temperature optima are often observed, as is production of zoosporangia and discharge of zoospores (Table 1). Variation among isolates is also observed with differences in oospore production, levels of spontaneous abortion, and germination frequency. Comparisons between isolates that were efficacious and nonefficacious in the field revealed that there is no correlation between efficacy and the particular cultural characteristics examined.

EXAMPLE 3

Root Colonization

When aseptically germinated tomato seed were colonized by P. oligandrum, in vitro, the mycelium was found primarily on the surface of the roots with no apparent visual symptoms of infection (e.g., necrosis or distortion of root morphology). When examined under the microscope, the fungus was found to occasionally penetrate an epidermal cell, but the hyphal growth was irregular in appearance and Recovery of P. oligandrum from roots of seedlings transplanted into the field was assessed by recovery of the seedlings from the field and gently removing adhering soil in water and plating on a medium that allows for identification of the biocontrol agent based on morphology. Low levels of root colonization by the biocontrol agent were observed.

In one trial, isolate 70-1 significantly reduced tomato damping-off, yet P. oligandrum was recovered at a frequency of only 0.1 colonies/cm of root. Even at the time of planting the frequency of recovery on selective medium was not high and was observed primarily on the tap root and crown regions of the seedling.

EXAMPLE 4

Formulations

Several different formulations have been evaluated for efficacy. A variety of different techniques can be used for production and formulation of biocontrol agents. Liquid cultures have been produced on a range of culture media containing readily available substrates such as homogenized vegetable juice. For example, in a preferred embodiment, production of oospores for conducting biocontrol trials can be done by growing cultures in a modified clarified V-8 juice broth culture (Ayers and Lumsden, 1975, Phytopathology 65:1094–1100). The medium is prepared by dissolving 1.5 g calcium carbonate in 200 ml of Cambells V-8 juice and pelleting the particulate matter by centrifugation. The supernatant is diluted with deionized water at a rate of 88 ml/l water and amended with cholesterol to a final concentration of 5 ppm. The medium is autoclaved prior to use.

Mycelial mats of the cultures are recovered on a sieve after 14 days growth at 25 C., rinsed in sterile water to remove medium and homogenized in a sterile blender. Mature thick walled oospores are counted with a hemacytometer and densities adjusted to desired levels prior to application to transplants. These have been formulated for application either directly to seeds or soil, mixed with a variety of materials for adhesion to seed surfaces, or encapsulated in sodium alginate. Liquid formulations have also been dried for addition to the soil either directly, mixed with kaolin dust, or coated onto perlite. Solid substrate fermentation using a variety of crop seeds also has been evaluated, U.S. Pat. No. 4,259,317.

1. Preferred Formulations

The preferred liquid preparation has been grown in several different media made from industrial byproducts or inexpensive, readily available components. Preferred dry formulations are either liquid fermentation biomass encapsulated in sodium alginate or pulverized dry fermentation products. Preliminary investigations on storage and survivability of inoculum have been conducted; with the dry formulation currently in use, a high level of survival is observed following eight weeks storage at room temperature.

2. Other Formulations

A. Wettable Powders

Wettable powders are water-dispersable compositions containing the active material, an inert solid extender, and one or more surfactants to provide rapid wetting and to prevent heavy flocculations when suspended in water.

The inert extenders which are preferred for use in the wettable powders of this invention containing the active compounds are of mineral or organic origin.

Extenders suitable for the wettable powder formulations of this invention are the natural clays, vermiculite, diatomaceous earth, and synthetic mineral fillers derived from silica and silicate. Most preferred filters for this invention are kaolinites, attapulgite clay, montmorillonite clays, synthetic silicas, synthetic magnesium silicate, and calcium sulfate dihydrate. A surface active agent can also be added to give a homogenous and stable formulation.

Among the more preferred surfactants are the nonionic and anionic types. They are most suitable for the preparation of dry, wettable products of this invention and dispersants. Occasionally a liquid, non-ionic compound which is primarily an emulsifier may serve as both wetter and dispersant.

Most preferred wetting agents are alkylbenzene and alkylnaphthalene sulfonates, sulfated fatty alcohols, amines, or acid amides, long chain esters of sodium isethionate, esters of sodium sulfosuccinate, sulfated or sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalene sulfonates, polymethylene bisnaphthalene sulfonate, and sodium-N-methyl-N-(long chain acid) taruates.

Wetting and dispersing agents in these preferred wettable powder compositions of the invention are usually present at concentrations of from about 0.5 weight percent to 5 weight percent. The inert extender then completes the formulation. Where needed, 0.1 weight percent of the extender may be replaced by a corrosion inhibitor or an anti-foaming agent or both.

Thus, wettable powder contains a corrosion inhibitor or an anti-foaming agent or both, the corrosion inhibitor should not exceed about 1 percent of the composition, and the anti-foaming agent should not exceed about 0.5 percent by weight of the composition, both replacing equivalent amounts of the inert extender.

B. Dusts

Dusts are dense powder compositions which are intended for application in dry form. Dusts are characterized by their free-flowing and rapid settling properties so that they are not readily windborne to areas where their presence is not desired. They contain primarily an active ingredient and a dense, free-flowing, solid extender. Their performance is sometimes aided by the inclusion of a wetting agent and convenience in manufacture frequently demands the inclusion of an inert absorptive grinding aid.

The wettable powder as described above can also be used in the preparation of dusts. While such wettable powders can be used directly in dust form, it is more advantageous to dilute them by blending with the dense dust diluent. In this manner, dispersing agents, corrosion inhibitors, and anti-foam agents may also be used as components of a dust.

Thus, the dust compositions of this invention can comprise from about 0.5 to 20.0 weight percent active ingredient, 5 to 25 weight percent filler, 0.0 to 1.0 weight percent wetting agent, and from about 30 to 90 weight percent dense, free-flowing extender, as these terms are used herein. Such dust formulations can contain, in addition, minor amounts of dispersants, corrosion inhibitors, and anti-foam agents derived from the wettable powders used to make the dust.

C. Emulsifiable Oils

Emulsifiable oils are usually solutions or suspensions of active material in non-water miscible solvents together with a surfactant and/or emulsifier.

For compositions of this invention, emulsifiable oil compositions can be made by mixing the active ingredient with an organic solvent and surfactant. Suitable solvents for the compositions of this invention are chlorinated solvents, water immiscible ethers, esters, or ketones alone or in admixture with aromatic hydrocarbons. Suitable surfactants are those ionic or non-ionic agents known to the art as emulsifying agents.

Emulsifying agents most suitable for the emulsifiable oil compositions of this invention are long chain alkyl or mercaptan polyethoxy alcohols, alkylaryl polyethoxy alcohols, sorbitan fatty acid esters, polyoxyethylene ethers with sorbitan fatty acid esters, polyethylene glycol esters with fatty rosin acids, fatty alkylol amide condensates, calcium and amine salts of fatty alcohol sulfates, oil soluble petroleum sulfonates, or preferably mixtures of these emulsifying agents should comprise from about 1 to 10 weight percent of the total composition. As described above, however, up to 5 parts of emulsifying agent for each part of active ingredient can be used.

Thus, emulsifiable oil compositions of the present invention can consist of from about 10 to 50 weight percent active ingredient, about 40 to 82 percent solvents, and about 1 to 10 weight percent emulsifier, as these terms are defined and used above.

D. Granules

Granules are physically stable, particulate compositions containing spores and/or mycelia of this invention which adhere to or are distributed through a basic matrix of a coherent, inert carrier with microscopic dimensions. In order to aid leaching of the active ingredient from the granule, a surfactant can be present.

The inert carrier is preferably of mineral origin, and suitable carriers are natural clays, some pyrophyllites and vermiculite. Suitable wetting agents can be anionic or nonionic.

For the granule compositions of this invention, most suitable carriers are to two types. The first are porous, absorptive pre-formed granules, such as preformed and screened granular attapulgite or heat expanded, granular, screened vermiculite. On either of these, a solution of the active agent can be sprayed and will be absorbed at concentrations up to 25 weight percent of the total weight. The second type are initially powdered kaolin clays, hydrated attapulgite, or bentonite clays in the form of sodium calcium, or magnesium bentonites. Water-soluble salts such as sodium salts may also be present to aid in the disintegrations of the granules in the presence of moisture. These ingredients are blended with the active component distributed uniformly throughout the mass. Such granules can also be made with 25 to 30 weight percent active component but more frequently a concentration of about 10 weight percent is desired for optimum distribution. The granular compositions of this invention are believed to be most useful in a size range of 15–30 mesh.

The most suitable wetting agents for the granular compositions of this invention depend upon the type of granule used. When pre-formed granules are sprayed with active material in liquid form, the most suitable wetting agents are non-ionic, liquid wetters miscible with the solvent. These are more generally known in the art as emulsifiers and comprise alkylaryl polyether alcohols, alkyl polyether alcohols, polyoxethylene sorbitan fatty acid esters, polyethylene glycol esters with fatty or rosin acids, fatty alkylol amide condensates, oil petroleum or vegetable oil sulfonates, or mixtures of these. Such agents will usually comprise up to about 5 weight percent of the total composition.

When the active ingredient is first mixed with a powdered carrier and subsequently granulated, liquid non-ionic wetters can still be used, but it is usually preferable to incorporate at the mixing stage one of the solid, powdered anionic wetting agents such as those previously listed for the wettable powders. Such agents should comprise about 0 to 2 percent of the total composition.

Thus, the preferred granular formulation of this invention comprises about 5 to 30 weight percent active material, about 0 to 5 weight percent wetting agent, and about 65 to 95 percent inert mineral carrier, as these terms are used herein.

EXAMPLE 5

Seed Coating Evaluations

The survivability of oospores from isolates efficacious in transplant trials when coated on the surface of tomato, cucumber, and soybean seeds was evaluated. Different types of adhering materials (carboxymethyl cellulose, sodium alginate, pelgel, nitracoat, and others) have been evaluated in these trials. Depending on the treatment that the biocontrol preparation received, significant levels of oospore survival were observed following 16 weeks storage at room temperature.

EXAMPLE 6

Molecular Identification of *Pythium oligandrum*

With more than 120 species in the genus Pythium, accurate identification of isolates can be difficult, particularly for species that share many morphological similarities. Therefore, unambiguous identification of isolates is preferred. The mitochondrial DNA (mtDNA) is an advantageous molecular marker for use with isolates of genus Pythium. The Pythium mtDNA is highly conserved within a species yet divergent between species to allow differentiation by RFLP analysis of even morphologically similar species. Detailed restriction maps have been constructed for 18 species in the genus and numerous geographically separated isolates of each species to evaluate both inter- as well as intra-specific variation of the genome. This research has supported the validity of using the mitochondrial DNA for taxonomic classification of species in the genus. By examining the mtDNA RFLPs and restriction maps, the isolates used as biocontrol agents described herein have been unequivocally identified as the nonphytopathogenic species *P. oligandrum.* The mitochondrial genome also has proved to be useful for construction of species, and in some cases isolate specific molecular markers. The organization of the mitochondrial genome in Pythium is unusual in that approximately 80% of the genome is comprised of an inverted repeat. The inverted repeats are separated by two single copy unique regions referred to as the small and large unique region (which is indicative of their relative sizes). It is predominantly in the small unique region where intraspecific variation in restriction maps for this species is observed (Genome 34:156–162). While not included in the previously cited reference, isolate 70-1 has a mtDNA restriction map similar to isolate 82-24. The use of sequences from the small unique region are useful for constructing probes with varying levels of species and isolate specificity (Phytopathology 81:742–746). Subsequent DNA sequence analysis has identified regions of sequence variation which should enhance the prospects for constructing isolate specific probes or PCR primers (See SEQ ID. NOs. 1–8).

EXAMPLE 7

Regions of DNA Sequence Variation Among Isolates of *Pythium oligandrum*

The small unique single copy region of the mitochondrial genome and adjacent inverted repeat (IR) regions were cloned and sequenced for several isolates of *P. oligandrum* (shown as SEQ ID NOs. 1–8). Sequence variation in these regions was found among all isolates except two (1985-5 [SEQ ID NO. 2] and 1986-41 [SEQ ID NO. 3]), providing a means for differentiating most isolates. A general outline of where these sequence variations were found follows.

Inverted Repeat

Among all isolates examined, sequence comparisons in the IR region are conserved with the following exceptions (data presented for only one arm of the inverted repeat):

1982-24 (SEQ ID NO. 1), 1986-41 (SEQ ID. NO. 3), 1985-5 (SEQ ID NO. 2), 17-1 (SEQ ID NO. 4), and 1986–43 (SEQ ID NO. 6) have an extra "A" at base 307.

1986-42 (SEQ ID NO. 6), 27-6 (SEQ ID NO. 7), and 30-1 (SEQ ID NO. 8) have an extra "A" at base 451.

1986-42 (SEQ ID NO. 6) has a deletion of 285 bp relative to isolate 17-1 (SEQ ID NO. 4) that removes a portion of the small unique and IR region, causing the IR region to be smaller than 17-1 by 234 bp. This deletion also is observed when comparing 1986-42 (SEQ ID NO. 6) to all other isolates, although the size of the deletion varies.

1982-24 (SEQ ID NO. 1), 1985-5 (SEQ ID NO. 2), and 1986-41 (SEQ ID NO. 3) have inverted repeats that are longer than the other isolates examined by approximately 774 bp (exact number varies depending on the isolate).

1986-41 (SEQ ID NO. 3) has an extra "AATA" in the IR relative to 1982-24 (SEQ ID NO. 1) and 1985–5 (SEQ ID NO. 2) starting at base 696.

Single Copy Small Unique Region

This region contains sequences that are most effective in exhibiting sequence uniqueness (except for 1985-5 [SEQ ID NO. 2] and 1986-41 [SEQ ID NO. 3], which are the same). The relative position of this region for each isolate is shown in Table 3.

TABLE 3

Positions of unique regions in isolates

| Isolate | SEQ ID NO. | position of unique region (base #s) |
|---|---|---|
| 1982-24 | 1 | 1278–2649 |
| 1985-5 | 2 | 1281–2653 |
| 1986-41 | 3 | 1281–2653 |
| 17-1 | 4 | 504–715 |
| 23-5 | 5 | 502–684 |
| 1986-42 | 6 | 270–664 |
| 27-6 | 7 | 504–? (region only partially sequenced to base 565) |
| 30-1 | 8 | 504–? (region only partially sequenced to base 612) |

Some specific regions of sequence variation are shown in Table 4.

TABLE 4

| SEQ ID NOs. | Regions of variation |
|---|---|
| 2 vs. 1 | base 1914 and 1910, respectively |
| 3 vs. 1 | base 1914 and 1910, respectively |
| 4 vs. 8 | base 562, 585, 608 |
| 4 (8) vs. 6 | bases 698–954 of SEQ ID NO. 4 deleted in SEQ ID NO. 6 |
|  | bases 500–550 of SEQ ID NO. 4 deleted in SEQ ID NO. 6 |
| 4 (8) vs. 5 | bases 500–550 of SEQ ID NO. 4 deleted in SEQ ID NO. 5 |
| 4 (8) vs. 7 | bases 500–550 of SEQ ID NO. 4 deleted in SEQ ID NO. 7 |
| 5 vs. | base 451, SEQ ID NO. 7 has an extra "A" |
|  | base 510 and 511, respectively |
|  | base 515 and 516, respectively |
|  | base 555 and 556, respectively |

EXAMPLE 8
Evaluation of Plant Pathogenicity

In his initial description of the species, Drechsler (1946) indicated the *P. oligandrum* could be isolated from necrotic tissue, but when tested for pathogenicity it did not infect plants. His conclusion was that this species was able to colonize tissue after it had been colonized by a pathogen. When coated on seed surfaces, *P. oligandrum* was found to be nonpathogenic in vitro and in vivo on 12 crop species representing six families (Martin and Hancock, 1987). When planted in fumigated soil, there was no reduction in shoot weight of stand counts. In addition, reduction of root densities was not observed when the plants were grown in field soil. Evaluations of pathogenicity also were conducted with several ornamental crops; none was observed. *Pythium oligandrum* also has been reported to be nonpathogenic on barley and oats (Kilpatrick, 1968, Plant Dis. Rep. 52:209–212; Bratoloveanu and Wallace, 1982, Biennial Report of the Waite Agricultural Research Institute 85:143 South Australia), pineapple (Klemmer and Nakano, 1964, Plant Dis. Rep. 48:848–852), cress (Al-Hamdani, 1982, Ph.D. dissertation, Dept. of Botany, University of Sheffield; Al-Hamdani et al., 1983, Plant Pathology 32:449–454; Lutchmeah and Cooke, 1984, Trans. Brit. Mycol. Soc. 83:696–700), carrot (Lutchmeah and Cooke, 1984), sugarbeet (O'Sullivan and Kavanagh, 1992, Plant Pathology 41:582–590), and several ornamental crops (Kelling, 1985, Nachrichtenblatt fur den Pflanzenschutz in der DDR 39:191–193). The colonization of tomato seedlings in vitro by *P. oligandrum* has been examined microscopically. Fungal hyphae grew over the surface of the root and occasionally penetrated a single cell in the top layer of the epidermis. However, hyphal growth within the plant cell was restricted with a knobby-like appearance and did not grow into adjacent cells.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. A method for controlling a fungal infestation in a plant comprising contacting said plant with an effective amount of a non-phytopathogenic *Pythium oligandrum* isolate selected from the group consisting of isolate 70-1 (ATCC 74395), isolate 25-6 (ATCC 74393) and isolate 30-1 (ATCC 74394).

2. The method, according to claim 1, wherein said fungus is a Pythium species.

3. The method, according to claim 1, wherein said method further comprises contacting said fungus with an agriculturally acceptable fungicide.

4. The method, according to claim 1, wherein said non-phytopathogenic organism has the characteristic of having activity at low-level root colonization wherein low-level root colonization is under 3 colonies recovered per centimeter of root.

5. The method, according to claim 4, wherein said low-level root colonization is approximately 0.1 colonies recovered per centimeter of root.

6. A method for protecting a plant from damping-off comprising administering an effective amount of a non-phytopathogenic *Pythium oligandrum* isolate selected from the group consisting of isolate 70-1 (ATCC 74395), isolate 25-6 (ATCC 74393) and isolate 30-1 (ATCC 74394) to said plant.

7. The method, according to claim 6, wherein said damping-off is caused by a phytopathogenic fungus.

8. The method, according to claim 7, wherein said phytopathogenic fungus is a Pythium species.

9. The method, according to claim 7, wherein said plant is a tomato plant.

10. The method, according to claim 6, wherein said plant to be protected is a potted seedling or transplant.

11. The method, according to claim 10, wherein said plant is a vegetable crop.

12. The method, according to claim 6, wherein the situs of the plant is soil surrounding roots of the plant.

13. The method, according to claim 12, wherein the soil is in a transplant pot.

14. A biologically pure non-phytopathogenic *Pythium oligandrum* isolate selected from the group consisting of isolate 70-1 (ATCC 74395), isolate 25-6 (ATCC 74393) and isolate 30-1 (ATCC 74394).

15. The isolate of claim 14, wherein said isolate is mycotoxic.

16. The isolate of claim 14, wherein the isolate is 70-1 (ATCC 74395).

* * * * *

UNITED STATES PATENT AND TRADEMARK OFFICE
CERTIFICATE OF CORRECTION

PATENT NO. : 5,961,971

DATED : October 5, 1999

INVENTOR(S) : Frank N. Martin

It is certified that error appears in the above-identified patent and that said Letters Patent is hereby corrected as shown below:

[57] Abstract, line 5: "applicable crops" should read --applicable to vegetable crops--.

Column 1, line 23: "fingicides" should read --fungicides--.

Column 5, line 62: "nbosomal" should read --ribosomal--.

Column 6, line 57: "*aphanidennatum*" should read --*aphanidermatum*--.

Column 13, line 31: "5 vs." should read --5 vs. 7--.

Signed and Sealed this

Twentieth Day of June, 2000

Q. TODD DICKINSON

*Attest:*

*Attesting Officer*      *Director of Patents and Trademarks*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 3926 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (C) INDIVIDUAL ISOLATE: 1982-24

(xi) SEQUENCE DESCRIPTION: SEQ ID NO:1:

```
CTGCAGCTGA ATCTGCTATA GGTTTAGCAA TAATGATTGT TTTTTTCAAA ATATATGGAG      60

ATATATCTAT TTATAAAATT AATCTATTAT CTTTATAGAT TAATTTTATA AGTATACATA     120

TAATTAATAA TATTTCTATT TCGTATTGAA ATAAAAATAT TTTTTATTAA CTTAAATTAA     180

AAAGCGAATA AAATTAAGAA AGCAATCATT AAACAGAATA AAGCAATAGA TTCAGTTAAA     240
```

```
GCGAAACCTA AAATAGCTGT TCTTGTTAAA TCTTGTTGTA AAGAAGGGTT TCTAGAAATA    300

CCTAAAACTA ATGAACTAAA TACTGAACCG ATACCGATAC CAGCACCTGC TAATCCAATA    360

GTAGCTAATC CAGCACCAAT AAATTTTGCA GATTGTAATA ACATATTATG TAATTAATTT    420

ATATCTTTTT AAAGATATAT AACTTTTAAA AAAAAATTAA AATGAAAATA CTTCTAATAA    480

GAATATATTT TATTATAAAT ATTAATTATT TATTTCTTAT TAAAATATTA TGATTATTTA    540

TTAAAGTAGA ATAAGGATTA CAATTTTCTG TTAAAAAAAT AAAACCTTTC TCTATTGAAG    600

AATTTTTTAT AGCTACTGTT TAATTAAAAA AGTTTATAAT TTAATTCTTT TATAGAACAT    660

TTAAAAAAAA ATATTATTAA TGGTAGAATT GAGAGAAATA CTTCTAATTT ACTTTATATT    720

AATAATATAG GAAATAATGA TATGATTGAT ACAAATACAA TTATTGAATT AAATAATTCA    780

ACTACTTCCG AAAGAAGAAT GGAATTTATG AATAGTATTA TACATCACGA AAATAATAAT    840

GAAAATCGTG CTCTATTAAT TGAACATAGT TCACCAGAAG TAAGGACTTA TTTACACGAG    900

TTATTAATTA GATCAGCAAA TAATTCAAAT ATAACTGAAG AGGTTTTATA TAGAATAGGA    960

AACATTTTCC TTTATACAAT ATCCAATTTA GATATAGACG GATTAGTTCT TAGAGATGTG   1020

ATTCAAAATA TGAGAGAATC TATGGTTATG TTTAACACAA ATCAAATTTA CTCTATACTT   1080

GAAAATCAAG TTAGTAACCA TAATCAATAT TTAGAAGAGA TTAGGTTAGC GAGTGAGGAA   1140

CATATTGATG AGCGCGTTCA AGAATTTCAT CGAGAAGTAG ATCAGAAAAT AGCTTTAAAT   1200

CGAAATGGAA TATTAGGATC AATGGCTTTA ACTTCTATAG GAGTTCCTCA AATTGTGAGT   1260

GGATTAGTAG CAAGATCGGT TTTATTTTGA AACTCTATCG AGTTTATTTT CTTTGAATTT   1320

TTCTAATATT TTATCCTCTA TTTTGTTATC GTTTTTGTCT ACTTTATATA TTAATAAAAT   1380

TTTTTTTCCT AATATTTCAA ATTTTGATTT ATTTTTGTAT ATATTTTCTT AAATTTTCTA   1440

ACTCTTTAGC ATCTTCTATT TGAAAAAAAT CAATTAATAA ACTAGCTTCA TCTCTTGTTA   1500

ACCCGTGAGT AGTTAGTGTT GTAAAAGGAC AAGCTGCTAC ATCTGACTGT GAGTTTATTC   1560

TCCAAAATTT AGCAATTAAT TTTTCTTCTT CATTTAAAAC GATTTCTGGT GAATTAAAAA   1620

ATTTCTCAAT AAGTTGTGTT ATCTCCAACG GTATTTCGTT TTCATTTAAA CACACATCAT   1680

TGAATATATA TATATTAAAA ATTAAGATTA ATATAAATAT TGTAATATTT TTATTTTTGA   1740

TTTCCATAAT TAATTGTTTT TATAATTAAA TTAGGTAAAG TAGTATCGAC GCCTAGTAGT   1800

CCTAAACATA TTATACCTCC ACCTATTAAT ATTTTCTTTT TCAATTTTTT AGCGTGTTCT   1860

TCACGTTCTT TTTGAAAAGT TTCTGCTCTC TCCTCTATTC CTTGAATAAA ATTATTTGTA   1920

ATTTCTTCTA GTTCTTGAGA ATTTTTGAGC TTTATTTCTT CTAAATATTT ATTAAAGTA    1980

GTTATTTGTT TATCTAAATC GATTGATATT TGATTTATGT TATAAATACA CATTGTTTCA   2040

CTTATCTTCT TCATAAAATC TCTTACTAAT AATCCCTCTA TTTCTAAATT CGATATCGTA   2100

TAAAGAAAAA TGTTTCCTAT TCGATAGAAA TCTTCTTCAG TTATATTTGA ATTAATTGCT   2160

GTTCTTCTTA ATAAATCATT TATATAAGTT CTCACGTGAG GTGAGCTATT TTCTATTAAT   2220

GATAAAAGAT TTTCACTATT ATTTTCGTGA TTTATAATAC TATTCATAAT CTCTAATCTT   2280

CTTTCAGAAG ATATGTGGTT ATTTAATTCA ATAATTGTTT GAGAATCAAT TGATTCTATA   2340

CCATTTAACT TTTTTATATA TGGTAATTTA TCTATATTAT TTAAAGATG ATGATTTATC    2400

TTATCTCTAA AACTTTCCTG TAAATTAAAA TTAGGAGGTT TTATTGGTGA ACCTTTTTCT   2460

TCAAATAATA AGTTGCCTAA TTTTAAGAAA TCTTCTGATT TAAAGTCTAT ATTATTGTTT   2520

ATCATATTTT ATTTATTAAA AGACTTAAGA GTATTATAAA ATAATTTAAT ACCTTCATCT   2580

AAAATATCCC TGAAACGGAT AATTCCTTCA GCCTCTGTTA ATTGAACTGT TGTAACAGGG   2640
```

-continued

```
GATATTACTG ATCTTGCTAC TAATCCACTC ACAATTTGAG GAACTCCTAT AGAAGTTAAA      2700

GCCATTGATC CTAATATTCC ATTTCGATTT AAAGCTATTT TCTGATCTAC TTCTCGATGA      2760

AATTCTTGAA CGCGCTCATC AATATGTTCC TCACTCGCTA ACCTAATCTC TTCTAAATAT      2820

TGATTATGGT TACTAACTTG ATTTTCAAGT ATAGAGTAAA TTTGATTTGT GTTAAACATA      2880

ACCATAGATT CTCTCATATT TTGAATCACA TCTCTAAGAA CTAATCCGTC TATATCTAAA      2940

TTGGATATTG TATAAAGGAA AATGTTTCCT ATTCTATATA AAACCTCTTC AGTTATATTT      3000

GAATTATTTG CTGATCTAAT TAATAACTCG TGTAAATAAG TCCTTACTTC TGGTGAACTA      3060

TGTTCAATTA ATAGAGCACG ATTTTCATTA TTATTTTCGT GATGTATAAT ACTATTCATA      3120

AATTCCATTC TTCTTTCGGA AGTAGTTGAA TTATTTAATT CAATAATTGT ATTTGTATCA      3180

ATCATATCAT TATTTCCTAT ATTATTAATA TAAAGTAAAT TAGAAGTATT TCTCTCAATT      3240

CTACCATTAA TAATATTTTT TTTTAAATGT TCTATAAAAG AATTAAATTA TAAACTTTTT      3300

TAATTAAACA GTAGCTATAA AAAATTCTTC AATAGAGAAA GGTTTTATTT TTTTAACAGA      3360

AAATTGTAAT CCTTATTCTA CTTTAATAAA TAATCATAAT ATTTTAATAA GAAATAAATA      3420

ATTAATATTT ATAATAAAAT ATATTCTTAT TAGAAGTATT TTCATTTTAA TTTTTTTTTA      3480

AAAGTTATAT ATCTTTAAAA AGATATAAAT TAATTACATA ATATGTTATT ACAATCTGCA      3540

AAATTTATTG GTGCTGGATT AGCTACTATT GGATTAGCAG GTGCTGGTAT CGGTATCGGT      3600

TCAGTATTTA GTTCATTAGT TTTAGGTATT TCTAGAAACC CTTCTTTACA ACAAGATTTA      3660

ACAAGAACAG CTATTTTAGG TTTCGCTTTA ACTGAATCTA TTGCTTTATT CTGTTTAATG      3720

ATTGCTTTCT TAATTTTATT CGCTTTTTAA TTTAAGTTAA TAAAAAATAT TTTTATTTCA      3780

ATACGAAATA GAAATATTAT TAATTATATG TATACTTATA AAATTAATCT ATAAAGATAA      3840

TAGATTAATT TTATAAATAG ATATATCTCC ATATATTTTG AAAAAAACAA TCATTATTGC      3900

TAAACCTATA GCAGATTCAG CTGCAG                                          3926
```

(2) INFORMATION FOR SEQ ID NO:2:

(i) SEQUENCE CHARACTERISTICS:
        (A) LENGTH: 3926 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: 1985-5

(xi) SEQUENCE DESCRIPTION: SEQ ID NO:2:

```
CTGCAGCTGA ATCTGCTATA GGTTTAGCAA TAATGATTGT TTTTTTCAAA ATATATGGAG       60

ATATATCTAT TTATAAAATT AATCTATTAT CTTTATAGAT TAATTTTATA AGTATACATA      120

TAATTAATAA TATTTCTATT TCGTATTGAA ATAAAAATAT TTTTTATTAA CTTAAATTAA      180

AAAGCGAATA AAATTAAGAA AGCAATCATT AAACAGAATA AAGCAATAGA TTCAGTTAAA      240

GCGAAACCTA AATAGCTGT TCTTGTTAAA TCTTGTTGTA AGAAGGGTT TCTAGAAATA       300

CCTAAAACTA ATGAACTAAA TACTGAACCG ATACCGATAC CAGCACCTGC TAATCCAATA      360

GTAGCTAATC CAGCACCAAT AAATTTTGCA GATTGTAATA ACATATTATG TAATTAATTT      420

ATATCTTTTT AAAGATATAT AACTTTTAAA AAAAAATTAA AATGAAAATA CTTCTAATAA      480

GAATATATTT TATTATAAAT ATTAATTATT TATTTCTTAT TAAAATATTA TGATTATTTA      540

TTAAAGTAGA ATAAGGATTA CAATTTTCTG TTAAAAAAAT AAAACCTTTC TCTATTGAAG      600
```

-continued

| | | | | | |
|---|---|---|---|---|---|
|AATTTTTTAT|AGCTACTGTT|TAATTAAAAA|AGTTTATAAT|TTAATTCTTT|TATAGAACAT| 660
|TTAAAAAAAA|ATATTATTAA|TGGTAGAATT|GAGAGAAATA|CTTCTAATTT|ACTTTATATT| 720
|AATAATATAG|GAAATAATGA|TATGATTGAT|ACAAATACAA|TTATTGAATT|AAATAATTCA| 780
|ACTACTTCCG|AAAGAAGAAT|GGAATTTATG|AATAGTATTA|TACATCACGA|AAATAATAAT| 840
|GAAAATCGTG|CTCTATTAAT|TGAACATAGT|TCACCAGAAG|TAAGGACTTA|TTTACACGAG| 900
|TTATTAATTA|GATCAGCAAA|TAATTCAAAT|ATAACTGAAG|AGGTTTTATA|TAGAATAGGA| 960
|AACATTTTCC|TTTATACAAT|ATCCAATTTA|GATATAGACG|GATTAGTTCT|TAGAGATGTG|1020
|ATTCAAAATA|TGAGAGAATC|TATGGTTATG|TTTAACACAA|ATCAAATTTA|CTCTATACTT|1080
|GAAAATCAAG|TTAGTAACCA|TAATCAATAT|TTAGAAGAGA|TTAGGTTAGC|GAGTGAGGAA|1140
|CATATTGATG|AGCGCGTTCA|AGAATTTCAT|CGAGAAGTAG|ATCAGAAAAT|AGCTTTAAAT|1200
|CGAAATGGAA|TATTAGGATC|AATGGCTTTA|ACTTCTATAG|GAGTTCCTCA|AATTGTGAGT|1260
|GGATTAGTAG|CAAGATCGGT|TTTATTTTGA|AACTCTATCG|AGTTTATTTT|CTTTGAATTT|1320
|TTCTAATATT|TTATCCTCTA|TTTTGTTATC|GTTTTTGTCT|ACTTTATATA|TTAATAAAAT|1380
|TTTTTTTCCT|AATATTTCAA|ATTTTGATTT|ATTTTTGTAT|ATATTTTCTT|AAATTTTCTA|1440
|ACTCTTTAGC|ATCTTCTATT|TGAAAAAAAT|CAATTAATAA|ACTAGCTTCA|TCTCTTGTTA|1500
|ACCCGTGAGT|AGTTAGTGTT|GTAAAAGGAC|AAGCTGCTAC|ATCTGACTGT|GAGTTTATTC|1560
|TCCAAAATTT|AGCAATTAAT|TTTTCTTCTT|CATTTAAAAC|GATTTCTGGT|GAATTAAAAA|1620
|ATTTCTCAAT|AAGTTGTGTT|ATCTCCAACG|GTATTTCGTT|TTCATTTAAA|CACACATCAT|1680
|TGAATATATA|TATATTAAAA|ATTAAGATTA|ATATAAATAT|TGTAATATTT|TTATTTTGA|1740
|TTTCCATAAT|TAATTGTTTT|TATAATTAAA|TTAGGTAAAG|TAGTATCGAC|GCCTAGTAGT|1800
|CCTAAACATA|TTATACCTCC|ACCTATTAAT|ATTTTCTTTT|TCAATTTTTT|AGCGTGTTCT|1860
|TCACGTTCTT|TTTGAAAAGT|TTCTGCTCTC|TCCTCTATTC|CTTGAATAAA|ATTATTTGTA|1920
|ATTTCTTCTA|GTTCTTGAGA|ATTTTTGAGC|TTTATTTCTT|CTAAATATTT|ATTAAAGTA|1980
|GTTATTTGTT|TATCTAAATC|GATTGATATT|TGATTTATGT|TATAAATACA|CATTGTTTCA|2040
|CTTATCTTCT|TCATAAAATC|TCTTACTAAT|AATCCCTCTA|TTTCTAAATT|CGATATCGTA|2100
|TAAAGAAAAA|TGTTTCCTAT|TCGATAGAAA|TCTTCTTCAG|TTATATTTGA|ATTAATTGCT|2160
|GTTCTTCTTA|ATAAATCATT|TATATAAGTT|CTCACGTGAG|GTGAGCTATT|TTCTATTAAT|2220
|GATAAAAGAT|TTTCACTATT|ATTTTCGTGA|TTTATAATAC|TATTCATAAT|CTCTAATCTT|2280
|CTTTCAGAAG|ATATGTGGTT|ATTTAATTCA|ATAATTGTTT|GAGAATCAAT|TGATTCTATA|2340
|CCATTTAACT|TTTTTATATA|TGGTAATTTA|TCTATATTAT|TTAAAAGATG|ATGATTTATC|2400
|TTATCTCTAA|AACTTTCCTG|TAAATTAAAA|TTAGGAGGTT|TTATTGGTGA|ACCTTTTTCT|2460
|TCAAATAATA|AGTTGCCTAA|TTTTAAGAAA|TCTTCTGATT|TAAAGTCTAT|ATTATTGTTT|2520
|ATCATATTTT|ATTTATTAAA|AGACTTAAGA|GTATTATAAA|ATAATTTAAT|ACCTTCATCT|2580
|AAAATATCCC|TGAAACGGAT|AATTCCTTCA|GCCTCTGTTA|ATTGAACTGT|TGTAACAGGG|2640
|GATATTACTG|ATCTTGCTAC|TAATCCACTC|ACAATTTGAG|GAACTCCTAT|AGAAGTTAAA|2700
|GCCATTGATC|CTAATATTCC|ATTTCGATTT|AAAGCTATTT|TCTGATCTAC|TTCTCGATGA|2760
|AATTCTTGAA|CGCGCTCATC|AATATGTTCC|TCACTCGCTA|ACCTAATCTC|TTCTAAATAT|2820
|TGATTATGGT|TACTAACTTG|ATTTTCAAGT|ATAGAGTAAA|TTTGATTTGT|GTTAAACATA|2880
|ACCATAGATT|CTCTCATATT|TTGAATCACA|TCTCTAAGAA|CTAATCCGTC|TATATCTAAA|2940
|TTGGATATTG|TATAAAGGAA|AATGTTTCCT|ATTCTATATA|AAACCTCTTC|AGTTATATTT|3000

```
GAATTATTTG CTGATCTAAT TAATAACTCG TGTAAATAAG TCCTTACTTC TGGTGAACTA      3060

TGTTCAATTA ATAGAGCACG ATTTTCATTA TTATTTTCGT GATGTATAAT ACTATTCATA      3120

AATTCCATTC TTCTTTCGGA AGTAGTTGAA TTATTTAATT CAATAATTGT ATTTGTATCA      3180

ATCATATCAT TATTTCCTAT ATTATTAATA TAAAGTAAAT TAGAAGTATT TCTCTCAATT      3240

CTACCATTAA TAATATTTTT TTTTAAATGT TCTATAAAAG AATTAAATTA TAAACTTTTT      3300

TAATTAAACA GTAGCTATAA AAAATTCTTC AATAGAGAAA GGTTTTATTT TTTTAACAGA      3360

AAATTGTAAT CCTTATTCTA CTTTAATAAA TAATCATAAT ATTTTAATAA GAATAAAATA      3420

ATTAATATTT ATAATAAAAT ATATTCTTAT TAGAAGTATT TTCATTTTAA TTTTTTTTTA      3480

AAAGTTATAT ATCTTTAAAA AGATATAAAT TAATTACATA ATATGTTATT ACAATCTGCA      3540

AAATTTATTG GTGCTGGATT AGCTACTATT GGATTAGCAG GTGCTGGTAT CGGTATCGGT      3600

TCAGTATTTA GTTCATTAGT TTTAGGTATT TCTAGAAACC CTTCTTTACA ACAAGATTTA      3660

ACAAGAACAG CTATTTTAGG TTTCGCTTTA ACTGAATCTA TTGCTTTATT CTGTTTAATG      3720

ATTGCTTTCT TAATTTTATT CGCTTTTTAA TTTAAGTTAA TAAAAAATAT TTTTATTTCA      3780

ATACGAAATA GAAATATTAT TAATTATATG TATACTTATA AAATTAATCT ATAAAGATAA      3840

TAGATTAATT TTATAAATAG ATATATCTCC ATATATTTTG AAAAAAACAA TCATTATTGC      3900

TAAACCTATA GCAGATTCAG CTGCAG                                          3926

(2) INFORMATION FOR SEQ ID NO:3:

(i) SEQUENCE CHARACTERISTICS:
        (A) LENGTH: 3933 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 1986-41

(xi) SEQUENCE DESCRIPTION: SEQ ID NO:3:

CTGCAGCTGA ATCTGCTATA GGTTTAGCAA TAATGATTGT TTTTTTCAAA ATATATGGAG        60

ATATATCTAT TTATAAAATT AATCTATTAT CTTTATAGAT TAATTTTATA AGTATACATA       120

TAATTAATAA TATTTCTATT TCGTATTGAA ATAAAAATAT TTTTTATTAA CTTAAATTAA       180

AAAGCGAATA AAATTAAGAA AGCAATCATT AAACAGAATA AAGCAATAGA TTCAGTTAAA       240

GCGAAACCTA AATAGCTGT TCTTGTTAAA TCTTGTTGTA AGAAGGGTT TCTAGAAATA         300

CCTAAAACTA ATGAACTAAA TACTGAACCG ATACCGATAC CAGCACCTGC TAATCCAATA       360

GTAGCTAATC CAGCACCAAT AAATTTTGCA GATTGTAATA ACATATTATG TAATTAATTT       420

ATATCTTTTT AAAGATATAT AACTTTTAAA AAAAAATTAA AATGAAAATA CTTCTAATAA       480

GAATATATTT TATTATAAAT ATTAATTATT TATTTCTTAT TAAAATATTA TGATTATTTA       540

TTAAAGTAGA ATAAGGATTA CAATTTTCTG TTAAAAAAAT AAAACCTTTC TCTATTGAAG       600

AATTTTTTAT AGCTACTGTT TAATTAAAAA AGTTTATAAT TTAATTCTTT TATAGAACAT       660

TTAAAAAAAA ATATTATTAA TGGTAGAATT GAGAGAAATA AATACTTCTA ATTTACTTTA       720

TATTAATAAT ATAGGAAATA ATGATATGAT TGATACAAAT ACAATTATTG AATTAAATAA       780

TTCAACTACT TCCGAAAGAA GAATGGAATT TATGAATAGT ATTATACATC ACGAAAATAA       840

TAATGAAAAT CGTGCTCTAT TAATTGAACA TAGTTCACCA GAAGTAAGGA CTTATTTACA       900

CGAGTTATTA ATTAGATCAG CAAATAATTC AAATATAACT GAAGAGGTTT TATATAGAAT       960
```

```
AGGAAACATT TTCCTTTATA CAATATCCAA TTTAGATATA GACGGATTAG TTCTTAGAGA    1020

TGTGATTCAA AATATGAGAG AATCTATGGT TATGTTTAAC ACAAATCAAA TTTACTCTAT    1080

ACTTGAAAAT CAAGTTAGTA ACCATAATCA ATATTTAGAA GAGATTAGGT TAGCGAGTGA    1140

GGAACATATT GATGAGCGCG TTCAAGAATT TCATCGAGAA GTAGATCAGA AAATAGCTTT    1200

AAATCGAAAT GGAATATTAG GATCAATGGC TTTAACTTCT ATAGGAGTTC CTCAAATTGT    1260

GAGTGGATTA GTAGCAAGAT CGGTTTTATT TTGAAACTCT ATCGAGTTTA TTTTCTTTGA    1320

ATTTTTCTAA TATTTTATCC TCTATTTTGT TATCGTTTTT GTCTACTTTA TATATTAATA    1380

AAATTTTTTT TCCTAATATT TCAAATTTTG ATTTATTTTT GTATATATTT TCTTAAATTT    1440

TCTAACTCTT TAGCATCTTC TATTTGAAAA AAATCAATTA ATAAACTAGC TTCATCTCTT    1500

GTTAACCCGT GAGTAGTTAG TGTTGTAAAA GGACAAGCTG CTACATCTGA CTGTGAGTTT    1560

ATTCTCCAAA ATTTAGCAAT TAATTTTYCT TCTTCATTTA AAACGATTTC TGGTGAATTA    1620

AAAAATTTCT CAATAAGTTG TGTTATCTCC AACGGTATTT CGTTTCATTT AAACACACAT    1680

CATTGAATAT ATATATATTA AAAATTAAGA TTAATATAAA TATTGTAATA TTTTTATTTT    1740

TGATTTCCAT AATTAATTGT TTTTATAATT AAATTAGGTA AAGTAGTATC GACGCCTAGT    1800

AGTCCTAAAC ATATTATACC TCCACCTATT AATATTTTCT TTTTCAATTT TTTAGCGTGT    1860

TCTTCACGTT CTTTTTGAAA AGTTTCTGCT CTCTCCTCTA TTCCTTGAAT AAAATTATTT    1920

GTAATTTCTT CTAGTTCTTG AGAATTTTTG AGCTTTATTT CTTCTAAATA TTTATTAAAA    1980

GTAGTTATTT GTTATCTAA ATCGATTGAT ATTTGATTTG TGTTATAAAT ACACATTGTT     2040

TCACTTATCT TCTTCATAAA ATCTCTTACT AATAATCCCT CTATTTCTAA ATTCGATATC    2100

GTATAAAGAA AAATGTTTCC TATTCGATAG AAATCTTCTT CAGTTATATT TGAATTAATT    2160

GCTGTTCTTC TTAATAAATC ATTTATATAA GTTCTCACGT GAGGTGAGCT ATTTTCTATT    2220

AATGATAAAA GATTTCACT ATTATTTTCG TGATTTATAA TACTATTCAT AATCTCTAAT     2280

CTTCTTTCAG AAGATATGTG GTTATTTAAT TCAATAATTG TTTGAGAATC AATTGATTCT    2340

ATACCATTTA ACTTTTTTAT ATATGGTAAT TTATCTATAT TATTTAAAAG ATGATGATTT    2400

ATCTTATCTC TAAAACTTTC CTGTAAATTA AAATTAGGAG GTTTTATTGG TGAACCTTTT    2460

TCTTCAAATA ATAAGTTGCC TAATTTTAAG AAATCTTCTG ATTTAAAGTC TATATTATTG    2520

TTTATCATAT TTTATTTATT AAAAGACTTA AGAGTATTAT AAAATAATTT AATACCTTCA    2580

TCTAAAATAT CCCTGAAACG GATAATTCCT TCAGCCTCTG TTAATTGAAC TGTTGTAACA    2640

GGGGATATTA CTGATCTTGC TACTAATCCA CTCACAATTT GAGGAACTCC TATAGAAGTT    2700

AAAGCCATTG ATCCTAATAT TCCATTTCGA TTTAAAGCTA TTTTCTGATC TACTTCTCGA    2760

TGAAATTCTT GAACGCGCTC ATCAATATGT TCCTCACTCG CTAACCTAAT CTCTTCTAAA    2820

TATTGATTAT GGTTACTAAC TTGATTTTCA AGTATAGAGT AAATTTGATT TGTGTTAAAC    2880

ATAACCATAG ATTCTCTCAT ATTTTGAATC ACATCTCTAA GAACTAATCC GTCTATATCT    2940

AAATTGGATA TTGTATAAAG GAAAATGTTT CCTATTCTAT ATAAAACCTC TTCAGTTATA    3000

TTTGAATTAT TTGCTGATCT AATTAATAAC TCGTGTAAAT AAGTCCTTAC TTCTGGTGAA    3060

CTATGTTCAA TTAATAGAGC ACGATTTTCA TTATTATTTT CGTGATGTAT AATACTATTC    3120

ATAAATTCCA TTCTTCTTTC GGAAGTAGTT GAATTATTTA ATTCAATAAT TGTATTTGTA    3180

TCAATCATAT CATTATTTCC TATATTATTA ATATAAAGTA AATTAGAAGT ATTTATTTCT    3240

CTCAATTCTA CCATTAATAA TATTTTTTTT TAAATGTTCT ATAAAGAAT TAAATTATAA     3300

ACTTTTTTAA TTAAACAGTA GCTATAAAAA ATTCTTCAAT AGAGAAAGGT TTTATTTTTT    3360
```

```
TAACAGAAAA TTGTAATCCT TATTCTACTT TAATAAATAA TCATAATATT TTAATAAGAA      3420

ATAAATAATT AATATTTATA ATAAAATATA TTCTTATTAG AAGTATTTTC ATTTTAATTT      3480

TTTTTTAAAA GTTATATATC TTTAAAAAGA TATAAATTAA TTACATAATA TGTTATTACA      3540

ATCTGCAAAA TTTATTGGTG CTGGATTAGC TACTATTGGA TTAGCAGGTG CTGGTATCGG      3600

TATCGGTTCA GTATTTAGTT CATTAGTTTT AGGTATTTCT AGAAACCCTT CTTTACAACA      3660

AGATTTAACA AGAACAGCTA TTTTAGGTTT CGCTTTAACT GAATCTATTG CTTTATTCTG      3720

TTTAATGATT GCTTTCTTAA TTTTATTCGC TTTTTAATTT AAGTTAATAA AAATATTTT       3780

TATTTCAATA CGAAATAGAA ATATTATTAA TTATATGTAT ACTTATAAAA TTAATCTATA      3840

AAGATAATAG ATTAATTTTA TAAATAGATA TATCTCCATA TATTTTGAAA AAACAATCA       3900

TTATTGCTAA ACCTATAGCA GATTCAGCTG CAG                                  3933

(2) INFORMATION FOR SEQ ID NO:4:

(i) SEQUENCE CHARACTERISTICS:
        (A) LENGTH: 1218 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: 17-1

(xi) SEQUENCE DESCRIPTION: SEQ ID NO:4:

CTGCAGCTGA ATCTGCTATA GGTTTAGCAA TAATGATTGT TTTTTTCAAA ATATATGGAG        60

ATATATCTAT TTATAAAATT AATCTATTAT CTTTATAGAT TAATTTTATA AGTATACATA       120

TAATTAATAA TATTTCTATT TCGTATTGAA ATAAAAATAT TTTTTATTAA CTTAAATTAA       180

AAAGCGAATA AAATTAAGAA AGCAATCATT AAACAGAATA AAGCAATAGA TTCAGTTAAA       240

GCGAAACCTA AAATAGCTGT TCTTGTTAAA TCTTGTTGTA AGAAGGGGTT TCTAGAAATA       300

CCTAAAACTA ATGAACTAAA TACTGAACCG ATACCGATAC CAGCACCTGC TAATCCAATA       360

GTAGCTAATC CAGCACCAAT AAATTTTGCA GATTGTAATA ACATATTATG TAATTAATTT       420

ATATCTTTTT AAAGATATAT AACTTTTAAA AAAAATTAA AATGAAAATA CTTCTAATAA        480

GAATATATTT TATTATAAAT ATTAATTATT TAAATTGTGT AAATCCACCA GAAATTTTAA       540

CTATTATAAA TATTGAAGAA CTTTTACTTA TATTTCTAAA TAATAATCTG AATTTAAACA       600

GTAGACCCTA TGAACCTTTA ATAATAGCTA TAAGAAATTT TTCAATAGAG AAAGGTTTTA       660

TTTTTTTAAT AGAAAATTGT AATTCTTATT TTACTTTAAT AAGAAATAAA TAATTAATAT       720

TTATAATAAA ATATATTCTT ATTAGAAGTA TTTTCATTTT AATTTTTTTT TAAAAGTTAT       780

ATATCTTTAA AAAGATATAA ATTAATTACA TAATATGTTA TTACAATCTG CAAAATTTAT       840

TGGTGCTGGA TTAGCTACTA TTGGATTAGC AGGTGCTGGT ATCGGTATCG GTTCAGTATT       900

TAGTTCATTA GTTTTAGGTA TTTCTAGAAA CCCTTCTTTA CAACAAGATT TAACAAGAAC       960

AGCTATTTTA GGTTTCGCTT TAACTGAATC TATTGCTTTA TTCTGTTTAA TGATTGCTTT      1020

CTTAATTTTA TTCGCTTTTT AATTTAAGTT AATAAAAAAT ATTTTATTT CAATACGAAA       1080

TAGAAATATT ATTAATTATA TGTATACTTA TAAAATTAAT CTATAAAGAT AATAGATTAA      1140

TTTTATAAAT AGATATATCT CCATATATTT TGAAAAAAC AATCATTATT GCTAAACCTA       1200

TAGCAGATTC AGCTGCAG                                                   1218

(2) INFORMATION FOR SEQ ID NO:5:
```

(i) SEQUENCE CHARACTERISTICS:
    (A) LENGTH: 1186 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (C) INDIVIDUAL ISOLATE: 23-5

(xi) SEQUENCE DESCRIPTION: SEQ ID NO:5:

```
CTGCAGCTGA ATCTGCTATA GGTTTAGCAA TAATGATTGT TTTTTTCAAA ATATATGGAG      60
ATATATCTAT TTATAAAATT AATCTATTAT CTTTATAGAT TAATTTTATA AGTATACATA     120
TAATTAATAA TATTTCTATT TCGTATTGAA ATAAAAATAT TTTTTATTAA CTTAAATTAA     180
AAAGCGAATA AAATTAAGAA AGCAATCATT AAACAGAATA AAGCAATAGA TTCAGTTAAA     240
GCGAAACCTA AAATAGCTGT TCTTGTTAAA TCTTGTTGTA AAGAAGGGTT TCTAGAAATA     300
CCTAAACTAA TGAACTAAAT ACTGAACCGA TACCGATACC AGCACCTGCT AATCCAATAG     360
TAGCTAATCC AGCACCAATA AATTTTGCAG ATTGTAATAA CATATTATGT AATTAATTTA     420
TATCTTTTTA AAGATATATA ACTTTTAAAA AAAAATTAAA ATGAAAATAC TTCTAATAAG     480
AATATATTTT ATTATAAATA TTGAAAAACT TTTATTTATA TTTTTAAATA ATGATCTGGA     540
TTTATACAGT AGATCCTATA AATCTTTAAT AGTAGTTATA AGAAATTCTT CAATAGAGAA     600
AGGTTTTATT TTTTCAATAG AAAATTGTAA TTCTTATTCT ATTTTAATAA ATAATCGTAA     660
TACTTTAATA AGAAATAAAT AATTAATATT TATAATAAAA TATATTCTTA TTAGAAGTAT     720
TTTCATTTTA ATTTTTTTTT AAAAGTTATA TATCTTTAAA AAGATATAAA TTAATTACAT     780
AATATGTTAT TACAATCTGC AAAATTTATT GGTGCTGGAT TAGCTACTAT TGGATTAGCA     840
GGTGCTGGTA TCGGTATCGG TTCAGTATTT AGTTCATTAG TTTAGGTATT TCTAGAAACC     900
CTTCTTTACA ACAAGATTTA ACAAGAACAG CTATTTTAGG TTTCGCTTTA ACTGAATCTA     960
TTGCTTTATT CTGTTTAATG ATTGCTTTCT TAATTTTATT CGCTTTTTAA TTTAAGTTAA    1020
TAAAAAATAT TTTTATTTCA ATACGAAATA GAAATATTAT TAATTATATG TATACTTATA    1080
AAATTAATCT ATAAAGATAA TAGATTAATT TTATAAAATAG ATATATCTCC ATATATTTTG    1140
AAAAAAACAA TCATTATTGC TAAACCTATA GCAGATTCAG CTGCAG                   1186
```

(2) INFORMATION FOR SEQ ID NO:6:

(i) SEQUENCE CHARACTERISTICS:
    (A) LENGTH: 934 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (C) INDIVIDUAL ISOLATE: 1986-42

(xi) SEQUENCE DESCRIPTION: SEQ ID NO:6:

```
TGCAGCTGAA TCTGCTATAG GTTTAGCAAT AATGATTGTT TTTTTCAAAA TATATGGAGA      60
TATATCTATT TATAAAATTA ATCTATTATC TTTATAGATT AATTTTATAA GTATACATAT     120
AATTAATAAT ATTTCTATTT CGTATTGAAA TAAAAATATT TTTTATTAAC TTAAATTAAA     180
AAGCGAATAA AATTAAGAAA GCAATCATTA AACAGAATAA AGCAATAGAT TCAGTTAAAG     240
CGAAACCTAA AATAGCTGTT CTTGTTAAAT CTTGTTGTAA AGAAGGGTTT CTAGAAATAC     300
```

```
CTAAAACTAA TGAACTAAAT ACTGAACCGA TACCGATACC AGCACCTGCT AATCCAATAG     360

TAGCTAATCC AGCACCAATA AATTTTGCAG ATTGTAATAA CATATTATGT AATTAATTTA     420

TATCTTTTTA AAGATATATA ACTTTTAAAA AAAAAATTAA AATGAAAATA CTTCTAATAA     480

GAATATATTT TATTATAAAT ATTGAAAAAC TTTTACTTAT ATTTTTAAAT AATGATCTGG     540

ATTTAGACAG TAGATCCTAT AAACCTTTAA TAGTAATTAT AAGAAATTCT TCAATAGAGA     600

AAGGTTTTAT TTTTTCAATA GAAAATTGTA ATTCTTATTC TACTTTAATA AACAATCATA     660

ATACTTTAAT AAGAACAGCT ATTTTAGGTT TCGCTTTAAC TGAATCTATT GCTTTATTCT     720

GTTTAATGAT TGCTTTCTTA ATTTTATTCG CTTTTTAATT TAAGTAATAA AAAAATATTT     780

TTATTTCAAT ACGAAATAGA AATATTATTA ATTATATGTA TACTTATAAA ATTAATCTAT     840

AAAGATAATA GATTAATTTT ATAAATAGAT ATATCTCCAT ATATTTTGAA AAAAACAATC     900

ATTATTGCTA AACCTATAGC AGATTCAGCT GCAG                                 934

(2) INFORMATION FOR SEQ ID NO:7:

(i) SEQUENCE CHARACTERISTICS:
        (A) LENGTH: 565 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (C) INDIVIDUAL ISOLATE: 27-6

(xi) SEQUENCE DESCRIPTION: SEQ ID NO:7:

CTGCAGCTGA ATCTGCTATA GGTTTAGCAA TAATGATTGT TTTTTTCAAA ATATATGGAG      60

ATATATCTAT TTATAAAATT AATCTATTAT CTTTATAGAT TAATTTTATA AGTATACATA     120

TAATTAATAA TATTTCTATT TCGTATTGAA ATAAAAATAT TTTTTATTAA CTTAAATTAA     180

AAAGCGAATA AAATTAAGAA AGCAATCATT AAACAGAATA AAGCAATAGA TTCAGTTAAA     240

GCGAAACCTA AAATAGCTGT TCTTGTTAAA TCTTGTTGTA AAGAAGGGTT TCTAGAAATA     300

CCTAAACTAA TGAACTAAAT ACTGAACCGA TACCGATACC AGCACCTGCT AATCCAATAG     360

TAGCTAATCC AGCACCAATA AATTTTGCAG ATTGTAATAA CATATTATGT AATTAATTTA     420

TATCTTTTTA AAGATATATA ACTTTTAAAA AAAAAATTAA AATGAAAATA CTTCTAATAA     480

GAATATATTT TATTATAAAT ATTGAAAAAC CTTTACTTAT ATTTTTAAAT AATGATCTGG     540

ATTTAGACAG TAGATCCTAT AAACC                                           565

(2) INFORMATION FOR SEQ ID NO:8:

(i) SEQUENCE CHARACTERISTICS:
        (A) LENGTH: 1183 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (C) INDIVIDUAL ISOLATE: 30-1

(xi) SEQUENCE DESCRIPTION: SEQ ID NO:8:

CTGCAGCTGA ATCTGCTATA GGTTTAGCAA TAATGATTGT TTTTTTCAAA ATATATGGAG      60

ATATATCTAT TTATAAAATT AATCTATTAT CTTTATAGAT TAATTTTATA AGTATACATA     120

TAATTAATAA TATTTCTATT TCGTATTGAA ATAAAAATAT TTTTTATTAA CTTAAATTAA     180
```

-continued

```
AAAGCGAATA AAATTAAGAA AGCAATCATT AAACAGAATA AAGCAATAGA TTCAGTTAAA    240

GCGAAACCTA AAATAGCTGT TCTTGTTAAA TCTTGTTGTA AAGAAGGGTT TCTAGAAATA    300

CCTAAACTAA TGAACTAAAT ACTGAACCGA TACCGATACC AGCACCTGCT AATCCAATAG    360

TAGCTAATCC AGCACCAATA AATTTTGCAG ATTGTAATAA CATATTATGT AATTAATTTA    420

TATCTTTTTA AAGATATATA ACTTTTAAAA AAAAAATTAA AATGAAAATA CTTCTAATAA    480

GAATATATTT TATTATAAAT ATTAATTATT TAAATTATAC AAATCCATCA GAAATTTTAA    540

CTGTTATAAA TATTAAAGAA CCTTTACTTA TATTTCTAAA TAATGACTGA ATTTAAACAG    600

TAGACCTTAT GNNNNNNNNN NNNNNNNNNN NNNNNNNNNN NNNNNNNNNN NNNNNNNNNN    660

NNNNNNNNNN NTAAATAATT AATATTTATA ATAAAATATA TTCTTATTAG AAGTATTTTC    720

ATTTTAATTT TTTTTTTAAA AGTTATATAT CTTTAAAAAG ATATAAATTA ATTACATAAT    780

ATGTTATTAC AATCTGCAAA ATTTATTGGT GCTGGATTAG CTACTATTGG ATTAGCAGGT    840

GCTGGTATCG GTATCGGTTC AGTATTTAGT TCATTAGTTT AGGTATTTCT AGAAACCCTT    900

CTTTACAACA AGATTTAACA AGAACAGCTA TTTTAGGTTT CGCTTTAACT GAATCTATTG    960

CTTTATTCTG TTTAATGATT GCTTTCTTAA TTTTATTCGC TTTTTAATTT AAGTTAATAA   1020

AAAATATTTT TATTTCAATA CGAAATAGAA ATATTATTAA TTATATGTAT ACTTATAAAA   1080

TTAATCTATA AAGATAATAG ATTAATTTTA TAAATAGATA TATCTCCATA TATTTTGAAA   1140

AAAACAATCA TTATTGCTAA ACCTATAGCA GATTCAGCTG CAG                     1183
```